(12) United States Patent
Maningas

(10) Patent No.: US 6,786,406 B1
(45) Date of Patent: Sep. 7, 2004

(54) MEDICAL PATHWAYS RAPID TRIAGE SYSTEM

(76) Inventor: Peter A. Maningas, 3317 McConnell Ave., Joplin, MO (US) 64804

( * ) Notice: Subject to any disclaimer, the term of this patent is extended or adjusted under 35 U.S.C. 154(b) by 19 days.

(21) Appl. No.: 10/402,554

(22) Filed: Mar. 28, 2003

(51) Int. Cl.[7] .............................................. G06F 17/60
(52) U.S. Cl. ..................................................... 235/385
(58) Field of Search .......................... 235/385; 705/1–3, 705/5, 8–9; 600/300

(56) References Cited

U.S. PATENT DOCUMENTS

| | | | |
|---|---|---|---|
| 5,255,187 A | * 10/1993 | Sorensen | .................... 600/300 |
| 5,823,948 A | * 10/1998 | Ross et al. | .................. 600/300 |
| 5,857,966 A | 1/1999 | Clawson | |
| 5,967,559 A | 10/1999 | Abramowitz | |
| 5,989,187 A | 11/1999 | Clawson | |
| 6,004,266 A | 12/1999 | Clawson | |
| 6,010,451 A | 1/2000 | Clawson | |
| 6,047,259 A | * 4/2000 | Campbell et al. | .............. 705/3 |
| 6,053,864 A | 4/2000 | Clawson | |
| 6,076,065 A | 6/2000 | Clawson | |
| 6,078,894 A | 6/2000 | Clawson et al. | |
| 6,106,459 A | 8/2000 | Clawson | |
| 6,139,494 A | 10/2000 | Cairnes | |
| 6,208,974 B1 | * 3/2001 | Campbell et al. | .............. 705/3 |
| 6,305,605 B1 | 10/2001 | Goetz et al. | |
| 6,383,135 B1 | 5/2002 | Chikovani et al. | |
| 6,383,185 B1 | * 5/2002 | Baumgart | ..................... 606/63 |
| 6,499,658 B2 | 12/2002 | Goetz et al. | |
| 6,638,218 B2 | * 10/2003 | Bulat | ......................... 600/300 |
| 2003/0212575 A1 | * 11/2003 | Saalsaa et al. | ................. 705/2 |

* cited by examiner

Primary Examiner—Karl D. Frech
Assistant Examiner—Edwyn Labaze
(74) Attorney, Agent, or Firm—Molly D. McKay (57) ABSTRACT

A computer based system for rapid triage of multiple patients in a hospital emergency department setting that allows flexibility in the order of entry of data. The system includes overlapping pathways for evaluating and assigning a criticality or triage level to a patient's condition based on the medical professional's observations about the patient's condition, the patient's age, the patient's vital signs, and a series of scripted questions and observations contained in an algorithm that is selected based on the patient's chief complaint. The system employs special triage algorithms for children. The computer interface provides waiting area and detailed patient information reports to an emergency department physician that are constantly updated with real time information on the criticality of each patient in the emergency department. The system also provides a permanent record of the triage process for each patient.

4 Claims, 10 Drawing Sheets

Algorithm – Microsoft Internet Explorer
File  Edit  View  Favorites  Tools  Help
Freeman Health System – Medical Pathways Triage System (BETA)

Chest Pain

"Do you have a history of heart disease?"

- Prior heart attack
- Angina
- Congestive heart failure
- Bypass surgery
- Balloon angioplasty
- Stent
- None of the above DOB
Gender
BP Systolic
BP Diastolic
Pulse
Respiratory Rate
Oxygen Saturation
Temperature
Temperature Route Comments/Notes

| Algorithm | Question | Response | Response Time |
|---|---|---|---|
| Chest Pain | Does the patient appear to be in moderate/severe distress? | None of the above | 1/19/2003 5:44:47 PM |
| Chest Pain | Does the patient exhibit any of the following? | None of the above | 1/19/2003 5:44:49 PM |
| Chest Pain | Is your chest pain a result of an injury to the chest within the past week? | No | 1/19/2003 5:44:51 PM |

Fig. 6

Medical Pathways Rapid Triage System
WAITING AREA
Main Page | Search Visits | View Waiting Area / Assign Room | Logout

| Triage Level | Visit Time | Chief Complaint | Last Name | First Name | | | |
|---|---|---|---|---|---|---|---|
| 2 | 9:44 AM | Chest Pain | | | LWOBS | Assign Disposition | View Report |
| 2 | 9:47 AM | Cough | | | LWOBS | Assign Disposition | View Report |
| 2 | 9:52 AM | Toothache/Jaw Pain (Non-Traumatic) | | | LWOBS | Assign Disposition | View Report |
| 4 | 8:18 AM | Pediatric Initial Screen (Age < 13) | | | LWOBS | Assign Disposition | View Report |
| 4 | 8:23 AM | Fever (Pediatric) | | | LWOBS | Assign Disposition | View Report |
| 2 | 9:47 AM | Pelvic Pain (Female) | | | LWOBS | Assign Disposition | View Report |

| | | | | | |
|---|---|---|---|---|---|
| untitled – paint | | | | | |
| Triage Report – Microsoft Internet Explorer | | | | | |
| File Edit View Favorites Tools Help | | | | | |

2 – EMERGENT

| | |
|---|---|
| DOB | 01/01/1934 69 Years |
| Gender | Male |
| BP Systolic | 164 |
| BP Diastolic | 84 |
| Pulse | 104 |
| Respiratory Rate | 16 |
| Oxygen Saturation | 98 |
| Temperature | 98 |
| Temperature Route | TYMPANIC |

Visit Date: 1/28/2003 1:30:17 PM
Fin. Number:
SSN: 111-11-1111
Last name:
First Name:

| Question | Response | Action | Log Time | Comment |
|---|---|---|---|---|
| Algorithm: Chest Pain<br>Does the patient appear to be in moderate/severe distress<br>– Pale<br>– Diaphoretic<br>– Clutching Chest<br>– Writhing/Pacing -- Unable to find comfortable position<br>– Unable to move without pain | Pale<br><br>Diaphoretic | | 1:30:20 PM | This observation requires Level 2 triage. |
| Is the patient too ill to continue? | No | | 1:30:26 PM | |
| Does the patient exhibit any of the following?<br>– Audible wheezing<br>– Difficulty talking in complete sentences<br>– Using accessory muscles of respiration | None of the above<br>None of the above | | 1:30:27 PM | |
| "Is your chest pain a result of an injury to the chest within the past week?" | No | | 1:30:42 PM | |
| "Do you have a history of heart disease?<br>– Prior heart attack<br>– Angina<br>– Congestive heart failure<br>– Bypass surgery<br>– Balloon angioplasty<br>– Stent" | Prior heart attack<br>Bypass surgery<br>Stent | Consider<br>– IV<br>– Oxygen<br>– Monitor<br>– EKG<br>– ASA<br>– NTG | 1:30:44 PM | This observation requires Level 2 triage. |

ELAPSED TIME TO TRIAGE: 29 sec
Triaged by: derekh

Finish and Print    Override Triage Level

Fig. 7

List of Algorithms by Category

Cardiorespiratory
Chest Pain
Cold Symptoms
Cough
Elevated Blood Pressure
Palpitations
Shortness of Breath

Constitutional
Cold Injury
Fever (Adult)
Heat Illness (Environmental)

Dermatology
Allergic Reaction
Derm (miscellaneous)
Insect Bite
Skin Rash/Abscess
Suture Removal

Ear, Nose and Throat (ENT)
Earache
Hearing Problems
Nosebleed (Epistaxis)
Sore Throat
Toothache/Jaw Pain (Non-traumatic)

Eye Problems

Gastrointestinal (GI)
Abdominal/Flank Pain
Difficulty Swallowing (Dysphagia)
Indigestion/Heartburn
Ingestion
Rectal Bleeding/Pain
Vomiting/Diarrhea

Genitourinary (GU)
Difficulty Voiding
Dysuria/Hematuria/Urinary Frequency or Urgency
GU Male (Genitourinary)

Musculoskeletal
Back Pain
Extremity Pain (Non-traumatic)
Neck Pain

Neuropsychiatric
Altered Mental Status
Dizziness
Headache
Psychiatric Problems (Not Altered Mental Status)
Seizure
Stroke/Weakness
Syncope/Near Syncope

OB/GYN
Gyn (Miscellaneous)
OB (Pregnancy > 20 wks)

Ob/GYN (Cont.)
Pelvic Pain (Female)
Sexual Assault
Vaginal Bleeding

Trauma
Assault
Burns
Extremity Injury
Facial Injury
Fall
Head Injury (Above the Neck)
Laceration (No other injuries)
MVA
Trunk Injury (Chest/Abdomen)

Miscellaneous
General Adult (Miscellaneous)
Needle Stick/Biohazard exposure
Prescription Refill

Fig. 8

Pediatric Algorithms

Pediatric Initial Screen (Age ≤ 13 yrs)

Constitutional
Heat Illness (Environmental)
Cold Injury
Fever (Pediatric)

Neuropsychiatric
Psychiatric Problems
Altered Mental Status
Dizziness
Headache
Seizure
Syncope

Eye Problems

Ear, Nose and Throat (ENT)
Earache
Nosebleed (Epistaxis)
Sore Throat
Toothache/Jaw Pain
Hearing Problems

Cardiorespiratory
Cold Symptoms
Cough
Chest Pain
Palpitations
Difficulty Breathing

Gastrointestinal (GI)
Abdominal/Flank Pain
Rectal Bleeding/Pain
Ingestion
Difficulty Swallowing
Vomiting/Diarrhea

Genitourinary (GU)
Dysuria
GU Male (Genitourinary)
Difficulty Voiding

OB/GYN
Gyn (Miscellaneous)

Musculoskeletal
Neck Pain
Back Pain
Extremity Pain (Non-traumatic)

Dermatology
Derm (Miscellaneous)
Insect Bite
Suture Removal
Allergic Reaction
Skin Rash/Abscess

Trauma
Assault
Burns
Trunk Injury (Chest/Abdomen)
Extremity Injury
Facial Injury
Fall
Head Injury (Above the Neck)
Laceration (No other injuries)
MVA

Fig. 9

MEDICAL PATHWAYS RAPID TRIAGE SYSTEM

BACKGROUND OF THE INVENTION

1. Field of the Invention

The present invention relates to a computer based system for rapid triage of patients in a hospital emergency department setting so that each patient is consistently and comprehensively evaluated upon entering the emergency department, regardless of the level of training of the personnel involved in the initial evaluation of the patient and regardless of the patient's problem. In thus providing a standardized method for evaluating and prioritizing patients based on the criticality of their conditions, the system provides more reliable and better prioritization of patient care in the emergency department setting. This system is designed to prevent hospital personnel from not recognizing the criticality of certain life threatening conditions and the resulting postponement of treatment based on an initial error in identifying the severity of the patient's problem. The system has special triage routines for children who face the greatest danger in triage evaluation due to their limited ability to communicate and due to the differences in their physiology as compared to adult patients.

The triage system includes a computer interface so that the emergency department physician has constant real time information on the criticality of each patient in the emergency department, thereby enabling the medical personnel to provide priority attention to those patients that have the most critical conditions. The computer interface of the triage system also provides the treating physician with a print out of the patient's information at the time the physician first sees the patient. That print out is a permanent record of the triage process for that patient.

2. Description of the Related Art

The normal procedure when a patient enters an emergency department is that either a nurse or a medical technician asks the patient a few questions about the patient's condition. They may or may not routinely take vital signs. Based on this initial evaluation of the patient's symptoms, and possibly vital signs, the medical professional then makes a decision about the criticality of the patient's condition and assigns a criticality or triage rating to each patient. Patients in the emergency department are then prioritized for receiving medical attention based on the medical professional's assigned critically of the patient's condition. This process is called triage which means "to sort", and the criticality rating is the triage level.

Currently, the decision regarding the criticality of the patient's condition can never be better than the experience and training level of the attending medical professional. If the attending medical professional is not well trained, is inexperienced, or for some other reason fails to ask the right questions, or if the patient is suffering from a condition that is rarely seen in the emergency department or a condition that exhibits symptoms that appear less severe than the actual critical nature of the patient's problem, the medical professional can easily make an error in assigning criticality to the patient's condition.

Emergency department triage is particularly difficult, even for well trained and experienced medical professionals when they operate without clear guidelines and without a well established decision tree that can be employed to make sure they ask the right questions every time and then properly evaluate the patient's condition based on the answers to their questions and based on their observations of the patient's physical condition. Even if the medical professional does a comprehensive nurse assessment, including obtaining the chief complaint, past medical and surgical history, medications and allergies, and spends a great deal of time acquiring this information, the medical professional may still wonder whether they made the right triage decision about a patient.

If the medical profession has triage guidelines that consist of a laundry list of clinical conditions parceled into triage levels, these lists are usually too long and difficult to remember so that they are rendered impractical to use on a patient-by-patient basis.

Errors in triage decisions can result in a patient who has a serious or even a life threatening condition that is badly in need of immediate medical care being allowed to remain in the emergency department waiting area without being treated while other less critical patients are given medical attention.

Obviously, these types of errors in triage of emergency department patients are undesirable from the patient's standpoint who may need immediate care and who can not get it because emergency department personnel did not properly identify the critical nature of his condition. These types of errors are also undesirable from the hospital's and physician's standpoints because both are morally dedicated to helping people and both are financially at risk for failing to provide the proper level of care to patients.

The present invention addresses these problems by providing a computer based triage system that helps eliminate most of the burden of triage decision making from the medical professional while still allowing the medical professionals to apply their observational skills and experience.

The present system is a stand alone, chief complaint based, algorithm driven triage system. First, this means it does not require integration with existing hospital computer systems, thereby eliminating the barriers to its use caused by problems and costs associated with integrating it with existing hospital computer systems. The present system is a stand alone, Web-based application that is easy to use, easy to access, and easy to maintain.

Second, the system is based on the patient's presenting chief complaint. Rarely does a patient come into an emergency department with a diagnosis in hand, but rather they present with a symptom or group of symptoms to the emergency department medical professional. The challenge for the medical professional is in differentiating between those who are not sick from those who are acutely ill, or even worse, those with potentially life-threatening conditions masquerading as a common, minor symptom.

Finally, the present system is driven by standardized algorithms. These algorithms are the heart of the system. For any given chief complaint given by a patient, there are a series of observations and questions that, based upon the observations made by the medical professional or answers given to the questions either by the patient or a person who comes to the emergency department with the patient, will lead down a specific decision tree or clinical pathway. These decision trees or clinical pathways are referred to as algorithms. The beauty of the system is that the intuitive clinical judgment used to spot potentially life threatening clinical conditions is built into the logic of the system. The system, by nature of the questions asked or information required, takes into consideration the patient's chief complaint, and their sex, age, vital signs, and pertinent past and present medical history in order to make a triage determination.

Even though this system is standardized and computerized, it is not infallible. Therefore, if medical professionals believe that a patient's condition is more critical than the triage level assigned by the system, the system can always be overridden to require a higher triage level for a patient, i.e. a triage level that would indicate that the patient is more critical than the triage level that was assigned to the patient by the system. However, as a conservative measure, the system can not be overridden to assign a lower triage level for a patient, i.e. a triage level that would indicate the patient is not as critical as the triage level that was assigned to the patient by the system.

The present system provides a clinical pathway for making observations and asking questions to allow a medical professional to quickly and accurately arrive at a final triage determination. The triage level is not established by diagnosis since there is no certain diagnosis at the time of triage but is based only upon the potential for certain clinical conditions based on the presenting clinical status of the patient and the patient's symptom complex. The system is designed to look at a patient as a whole, including the patent's physical appearance, age, sex, vital signs, pertinent past and present medical history, and presenting complaint, in making a triage determination.

The system employs a five tier triage scale consisting of levels I, II, III, IV, and V that are referred to respectively as immediate, emergent, urgent, semiurgent, and non-urgent. Level I conditions are life threatening and require immediate medical attention and intervention. Level II conditions are potentially life threatening and require emergent medical attention. Level III conditions may develop into a serious problem unless urgent medical evaluation and intervention is received. Level IV conditions are semi-urgent and may benefit from intervention to prevent deterioration or complications. Finally, Level V conditions are non-urgent conditions that are minor and could be delayed or deferred to other areas of the health care system with little risk of significant deterioration.

This system does not propose to dictate clinical standards for the specific time periods a patient needs to be evaluated and treated for any given triage level. Decisions regarding the time to be seen are entirely the decision of the local medical community and existing or future national guidelines. Also, this system does not propose in which area of an emergency department that patients should be seen or by whom. Where a patient with a particular triage level needs to be taken care of and who should supply that care is a decision that is best left to the individual hospital.

SUMMARY OF THE INVENTION

The present invention is a computer based system for rapid triage of patients in a hospital emergency department setting so that each patient is consistently and comprehensively evaluated upon entering the emergency department, regardless of the level of training of the personnel involved in the initial evaluation of the patient and regardless of the patient's problem. The system is to be employed by emergency department medical professionals to provide a standardized method for evaluating and prioritizing patients based on the criticality of their conditions, thus providing a more reliable and better prioritization of patient care in the emergency department setting.

This system includes overlapping pathways for evaluating and assigning a triage level to a patient's condition based on the medical professional's observations about the patient's condition, the patient's age, the patient's vital signs, and a series of scripted questions and observations in a selected algorithm that is selected based on the patient's chief complaint. The system is designed to prevent hospital personnel from not recognizing the criticality of certain life threatening conditions and the resulting postponement of treatment based on an initial error in identifying the severity of the patient's problem. The system also allows the medical profession flexibility in the order in which the steps of triage are done and entered into the system, including the ability to postpone completion of triage on one patient so that triage can be begun on one or more other patients.

The system has special triage routines for children who face the greatest danger of misevaluation in triage due to their limited ability to communicate and due to the differences in their physiology as compared to adult patients.

The triage system includes a computer interface so that the emergency department physician has constant real time information on the criticality of each patient in the emergency department, thereby enabling the medical personnel to provide priority attention to those patients that have the most critical conditions. The computer interface of the triage system also provides the treating physician with a print out of the patient's information at the time the physician first sees the patient. That print out is a permanent record of the triage process for that patient.

BRIEF DESCRIPTION OF THE DRAWINGS

FIGS. 1-A, 1-B, 1-C, 1-D, and 1-E show a flow chart detailing a medical pathways rapid triage system according to a preferred embodiment of the present invention.

FIG. 5 is an algorithm screen from the present system

FIG. 6 is a waiting area screen from the present system.

FIG. 8 is a list of algorithms used in the present system shown ordered by category.

FIG. 9 is a list of pediatric algorithms used in the present system.

DETAILED DESCRIPTION OF THE PREFERRED EMBODIMENT

THE INVENTION

Figure 1:
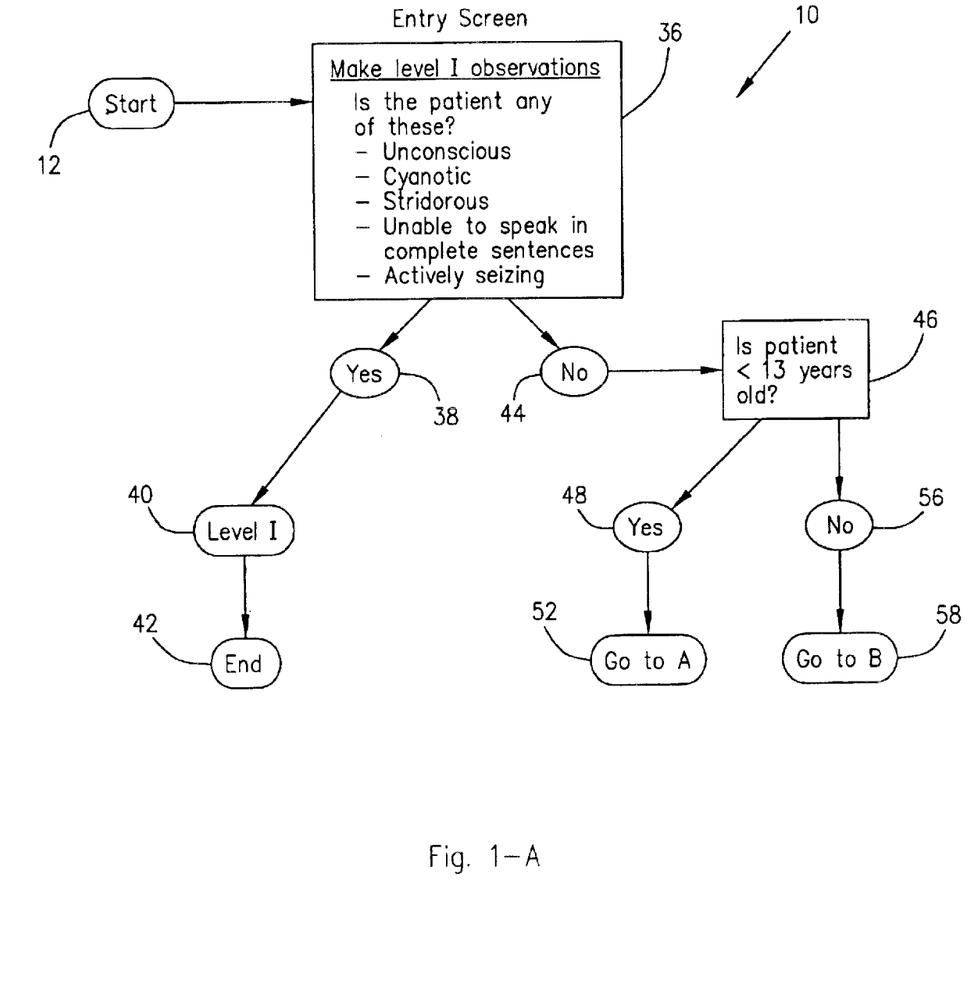

Referring now to the drawings and initially to FIGS. 1-A through 1-E, there is illustrated a flow chart that details a medical pathways rapid triage system 10 according to a preferred embodiment of the present invention. The system 10 is a computer based program for rapid triage of patients in a hospital emergency department setting so that each patient is consistently and comprehensively evaluated upon entering the emergency department, regardless of the level of training of the personnel involved in the initial evaluation of the patient and regardless of the patient's problem. The system 10 is to be employed by emergency department medical professionals to provide a standardized method for evaluating and prioritizing patients based on the criticality of their conditions, thus providing a more reliable and better prioritization of patient care in the emergency department setting.

Figure 2:
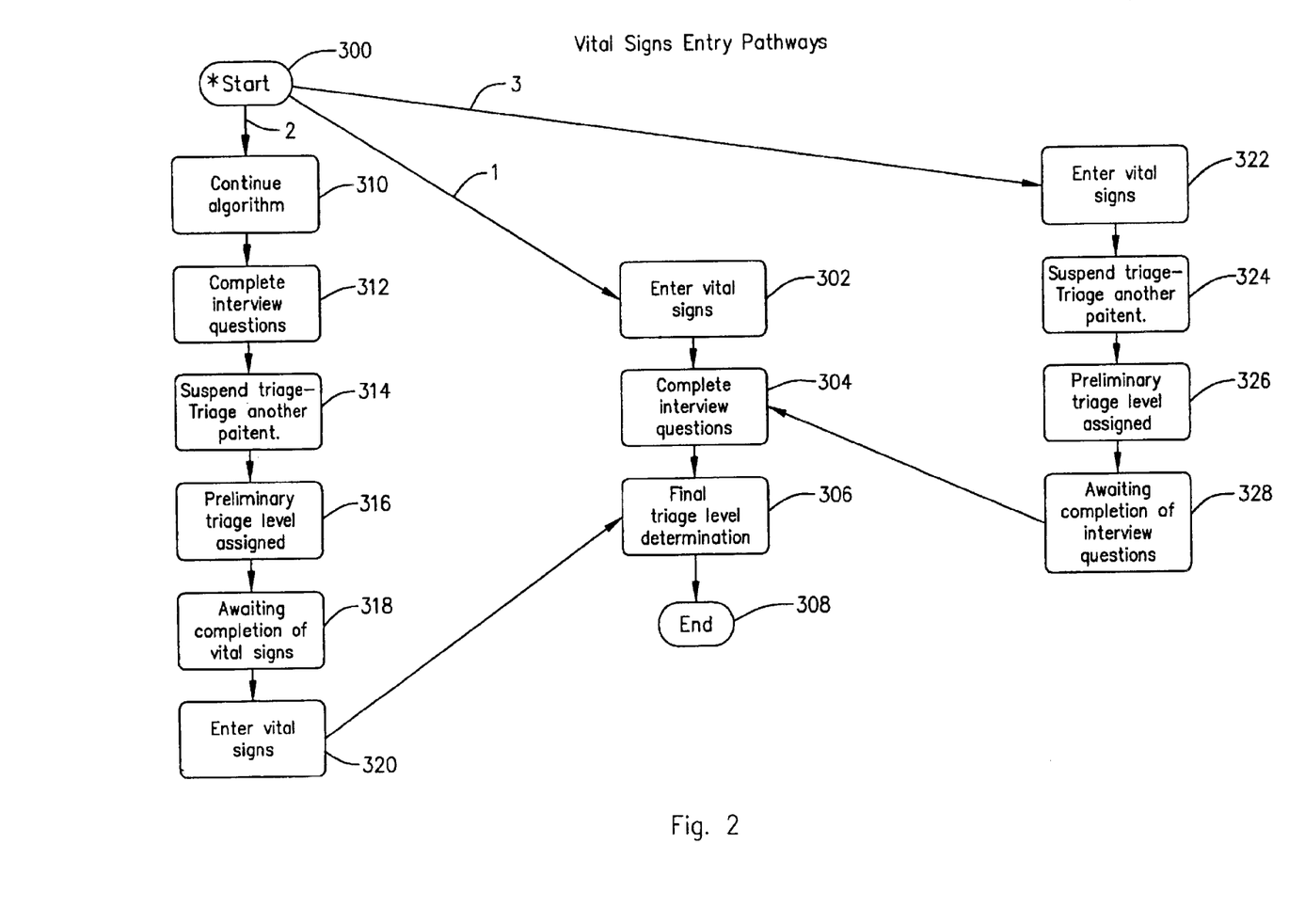
FIG. 2 is a diagram showing the three alternate pathways that triage data entry can take employing the present system.

FIG. 2 is another flow chart that shows three different pathways that data entry into the system 10 can follow, illustrating the flexible nature of the system 10.

Figure 3:
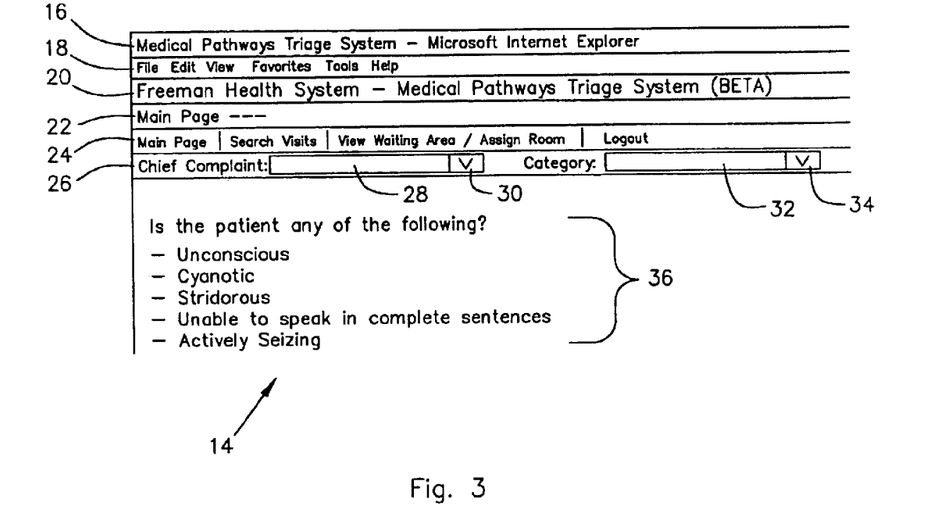
FIG. 3 is an entry screen of the present system.

Beginning with the start box 12 of FIG. 1A, the system 10 will be described. The first computer screen that appears in the program is the entry screen 14. A typical entry screen 14 is illustrated in FIG. 3. Several heading lines are provided at the top of the entry screen 14. The upper heading line includes the program name, and the second heading line 18 includes standard commands. The third heading line 20 includes the users name, and the fourth heading line 22 identifies the page or screen of the program that is appearing on the screen, i.e. the main page which is also called the entry screen 14. The fifth heading line 24 provides choices that allow the user to jump to different screens in the program, i.e. Search Visits or View Waiting Area/Assign Room, or to logout of the program. Because the program stores all previously entered visits to the emergency department by a patient, the Search Visits screen can be used to access previous triage reports sorted by patient name, social security number, date, triage level or chief complaint.

The sixth line 26 on the entry screen 14 shows a chief complaint box 28 for entering a patient's chief complaint. The choices that are available for entry into the chief complaint box 28 are listed in alphabetical order in a drop down list that can be accessed by clicking on the arrow button 30 located at the end of the chief complaints box 28. The medical professional may also choose to select a chief complaint by using the category box 32 located on the sixth line 26 following the arrow button 30. The categories are body systems with those chief complaints that are associated with that particular body system being listed under the body system heading. The choices of categories can be scrolled using a second arrow button 34 located at the end of the categories box 32. The chief complaint may then be selected from a list under the appropriate category or body system.

Under the headings, the main page or entry screen 14 of the system 10 initially lists level 1 observations 36 that the medical professional is required to make relating to a patient's condition. These observations are shown as box 36 in FIG. 1-A. They are called level 1 observations 36 because the presence of any one of these conditions indicates a criticality level of 1 for purposes of triage. The medical professional must choose any of the applicable level 1 observations 36 if they are observed in the patient. If any of the level 1 observations 36 are made as indicated by box 38 in FIG. 1-A, the patient is immediately assigned a level 1 triage priority, as shown in box 40, and the triage process is ended for that patient, as shown in box 42.

The system 10 has special triage routines for children who, due to their limited ability to communicate and due to the differences in their physiology as compared to adult patients, face the greatest danger of misevaluation in triage. If the medical professional says no, as shown by box 44, to the question of whether the patient has any of the level 1 observations 36, the next inquiry as shown in box 46, is whether the patient is less than thirteen (13) years old. If the answer to this question is yes, as shown in box 48, the pediatric initial screening algorithm 50 is begun, as shown by the Go to A box 52 in FIG. 1-A and the A box 54 in FIG. 1-B. If the answer to this less than thirteen (13) years old question 46 is no, as shown by box 56, the process continues, as shown in Go to B box 58 in FIG. 1-A and box B 60 in FIG. 1-C.

The discussion that follows will first describe the adult process beginning at box B 60 of FIG. 1-C, and, following that discussion, discussion describing the pediatric initial screening algorithm 50 will begin at box A 54 of FIG. 1-B.

Adult Process

Beginning at B box 60 of FIG. 1-C, the data entry process continues by identifying and entering into the computer the patient's chief complaint, as shown in box 28 of FIG. 1-C. The medical profession enters the patient's chief complaint in box 28 of the entry screen 14, as shown in FIG. 3. Entry of the patient's chief complaint allows the program to select and initiate one of approximately fifty six (56) specific algorithms that are specifically designed around the chief complaint of these patients who are 13 and older, as shown in box 62. A listing of these algorithms, listed by category, is shown in FIG. 8.

Figure 4:
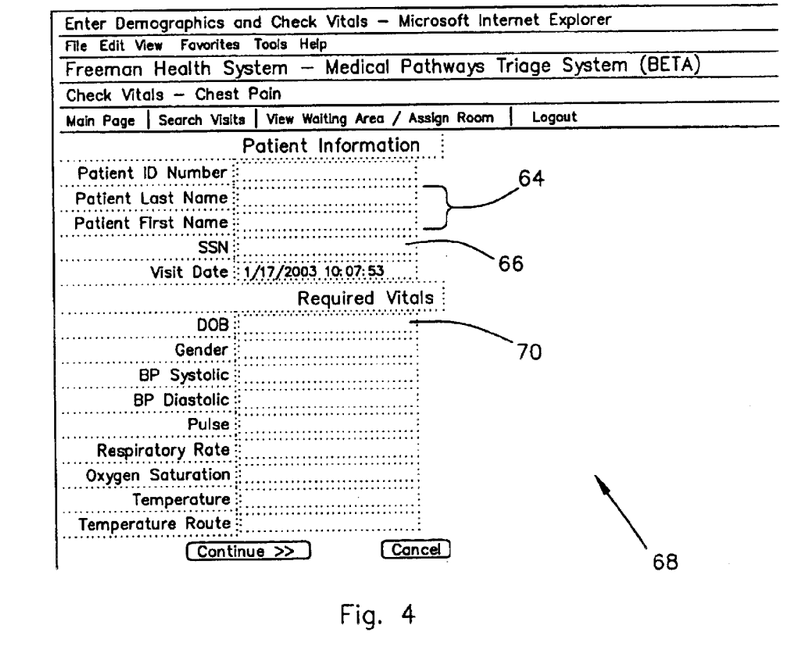
FIG. 4 is a vital signs screen of the present system.

Next, at least one identifier for the patient must be entered into the computer, i.e. either the patient's name 64 or their social security number (SSN) 66, as shown the vital signs screen 68 shown in FIG. 4. The identifier 64 or 66 is used by the computer to track the triage process for that patient. Also, the patient's date of birth (DOB) 70 must also be entered. This is shown in box 72 in FIG. 1-C. The vital signs screen 68 is shown where patient information is entered into the computer and where the patient's vital signs are next entered into the computer, as shown in box 74 of FIG. 1-C.

There is a * located between box 72 and 74 indicating that from this point forward in the process there are several optional routes for performing the remaining steps of the triage process. Those optional routes are illustrated in FIG. 2 and will be described in more detail hereafter. Continuing at box 74 of FIG. 1-C, after the patient's vital signs are entered into the computer, the computer evaluates the vital signs information in a series of logic steps that may allow the program to assign a triage level to the patient or may lead the patient through further interview questions before a triage level is assigned.

The remaining boxes of FIG. 1-C show the logic used by the program to assign a triage level to the patient based on the patient's vital signs. These boxes are separated into two groups by broken line 76, with the boxes located above broken line 76 relating to primary vital signs, i.e. oxygen saturation and systolic blood pressure, and the boxes located below broken line 76 relating to secondary vital signs, i.e. heart rate and respiratory rate.

As shown in box 78, the first question is whether the patient's systolic blood pressure is abnormally low, i.e. less than or equal to 90 mm Hg. As shown in boxes 80A and 80B, the second question is whether the patent's oxygen saturation is low, i.e. less than or equal to 90%. These first two questions relate to the primary vital signs. Significant alterations in these primary vitals signs usually indicate a decompensated physiological state requiring prompt medical attention.

The next two questions, the third and fourth questions relate to the secondary vital signs. Alterations in these secondary vital signs frequently are a result of the body's attempts at compensating for some physiologic abnormality. As shown in boxes 82A and 82B, the third question is whether the patient's heart rate or pulse is abnormally high, i.e. greater than or equal to 120 beats/minute, or abnormally low, i.e. less than or equal to 50 beats/minute. As shown in boxes 84A, 84B, and 84C, the fourth question is whether the patient's respiratory rate is abnormally high, i.e. greater than or equal to 28 respirations/minute, or abnormally low, i.e. less than or equal to 8 respirations/minute.

A yes answer, shown in box 86, to the first primary vital signs question 78 in combination with a yes answer, shown in box 88, to the second primary vital signs question 80A, will immediately result in a level 1 triage assignment, as shown in box 90, since these primary vital signs signify a decompensated cardio-respiratory status requiring immediate medical intervention. After assignment of triage level 1 in box 90, the triage ends for that patient, as indicated by box 92.

A combination of a yes answer 86 to primary vital signs question 78, a no answer 100 to the other primary vital signs question 80A, and a yes answer 96 to the secondary vital signs question 82A also will result in assignment of triage level 1, as indicated in box 90, and an end to the triage for that patient, as indicated by box 92.

Likewise, a combination of a no answer 102 to the primary vital signs question 78, a yes answer 94 to primary vital signs questions 80B, and a no answer 104 to secondary vital signs question 82A, and a yes answer 98 to secondary vital signs question 84A also will result in assignment of triage level 1, as indicated in box 90, and an end to the triage for that patient, as indicated by box 92.

Likewise, a combination of a no answer 102 to primary vital signs question 78, a yes answer 94 to primary vital signs question 80B, and a yes answer 96 to secondary vital signs questions 82A will result in assignment of triage level 1, as indicated by box 90, and an end to the triage for that patient, as indicated by box 92.

On the other hand, a combination of a yes answer 86 to primary vital signs question 78, a no answer 100 to primary vital signs question 80A, a no answer 104 to secondary vital signs question 82A, and a no answer 106 to secondary vital signs question 84A will result in assignment of a triage level of no less than Level II, as indicated by box 108, since this combination indicates a potentially life threatening clinical status that requires emergent intervention to avoid deterioration. From there, the process will continue, as indicated by the Go to D box 110 shown on FIG. 1-C and the D box 112 shown on FIG. 1-E.

Likewise, a combination of a no answer 102 to primary vital signs question 78, a yes 94 to primary vital signs question 80B, a no answer 104 to secondary vital signs question 82A, and a no answer 106 to secondary vital signs question 84A will also result in assignment of a triage level of no less than Level II, as indicated by box 108. From there, the process will continue, as indicated by the Go to D box 110 shown on FIG. 1-C and the D box 112 shown on FIG. 1-E.

Likewise, no answers 102 and 114 to both of the primary vital signs questions 78 and 80B, respectively, in combination with yes answers 116 and 118 to both of the secondary vital signs questions 82B and 84B, respectively, will also result in assignment of a triage level of no less than Level II, as indicated by box 108, and the process will continue, as indicated by the Go to D box 110 shown on FIG. 1-C and the D box 112 shown on FIG. 1-E.

The combination of two no answers 102 and 114 to both of the primary vital signs questions 78 and 80B, respectively, a yes answer 116 to the secondary vital signs question 82B, and a no answer 124 to secondary vital signs question 84B will result in assignment of a triage level of no less than Level III, as indicated by box 126, since this indicates a condition that could potentially develop into a serious medical problem, thus requiring urgent medical evaluation. The process will continue, as indicated by the Go to D box 110 shown on FIG. 1-C and the D box 112 shown on FIG. 1-E.

Likewise, the combination of two no answers 102 and 114 to both of the primary vital signs questions 78 and 80B, respectively, a no answer to 122 to secondary vital signs question 82B, and a yes answer 120 to the secondary vital signs question 84C will result in assignment of a triage level of no less than Level III, as also indicated by box 126. The process will continue, as indicated by the Go to D box 110 shown on FIG. 1-C and the D box 112 shown on FIG. 1-E.

Finally, if no answers 102, 114, 122, and 128 are given to all of the vital signs questions 78, 80B, 82B, and 84C, respectively, a preliminary level assignment for the patient will not be made at this time, and the process will continue, as indicated by the Go to D box 110 shown on FIG. 1-C and the D box 112 shown on FIG. 1-E.

Beginning with D box 112 on FIG. 1-E, the medical professional then must make level II observations, as indicated by box 130. These observations include and inquiry about whether the patient is experiencing alteration in respiratory status, alteration in mental status, or painful distress. If the answer to the level II observations is yes, as indicated by box 132, the next inquiry, as shown in box 134, is whether the patient is too sick to continue the triage process.

If the answer to the question of box 134 is yes, as indicated by box 136, a level II priority is assigned to the patient, as shown by box 138, and the triage process in ended for that patient, as indicated by box 140. If the answer to box 134 is no, as indicated by box 142 or if the answer to box 130 level II observations is no, as also indicated by box 142, then the process continues at box 144.

Box 144 represents a series of interview questions and observations that are dictated by the algorithm selected in box 62 of FIG. 1-C based on the chief complaint determined in box 28 of FIG. 1-C. These questions are standardized, scripted and appear in blue and quotation marks. This is in contrast to the observations required of the person performing the triage which appear in black. The answer the patient gives to these questions results in a specific triage pathway being followed.

The algorithms or pathways overlap so that if the answers indicate that the wrong algorithm was initially selected, the program will automatically transfer to and continue to follow the proper pathway or algorithm. This transfer is done seamlessly to the user. However, the user can always look at the fourth line heading 22 of the computer screen to tell the algorithm that is in current use. FIG. 5 shows a chest pain algorithm screen 152 with the chest pain algorithm 178 listed in the heading of the fourth heading line 22 of the algorithm screen 152 and below the headings is a typical question 154 that is asked in the algorithm and possible answers 156.

The questions, answer, and observations of each algorithm are scripted so that the medical professional will not miss a question or a possible important answer or observation. The questions and observations help to further elucidate the nature of the patient's problem and the urgency for evaluation. The medical professional reads each scripted question exactly as it appears on the screen and reads all of the answers of the scripted interview process.

At the bottom of the algorithm screen 152 shown in FIG. 5, as shown by numeral 158, appears a listing of each of the questions 154 that have been asked of the patient, the algorithm 151 from which that question originated, each of the answers 156 the patient gave to those questions along with the specific date and time that the answers were entered into the computer. This listing 158 enables the medical professionals to quickly scan the patient's responses and also provides a complete record of the patient's triage.

Multiple descriptive answers 156 to each question 154 are possible with the program, and all answers 156 that apply to a patient should be selected. The user can return to the question 154 to correct an answer 156 to that question 154 by clicking on the back button that is located in the second heading 18, or alternately, by clicking on the question 158 at the bottom of the page which is a hyperlink to that question 154. When completing the questions, a selection of "none of the above" 155 is an option available for selection. However, if one of the other descriptive answers 156 is to the same question 154 is selected, the "none of the above" option 155 is removed from the screen as an option, i.e. it will disappear from the screen 152, and a continue button will appear in its place. Pressing either the "none of the above" option 155 or the continue button will advance the program to the next question in the algorithm. Therefore, if one of the descriptive answers 156 was selected when the patient really has none of the descriptive answers 156, the algorithm 178 will have to be started over by clicking on the back button until the vital signs screen 68 appears and then reclicking the continue button.

Also, as shown in FIG. 5, the right hand side of the screen 152 includes the patient's vital sign information 160. Displaying the patient's vital signs 160 on the same screen 152 with the interview questions 154 allows the medical professionals flexibility to enter or correct data for vital signs in whatever order they desire, as will be further explained hereafter.

As shown in box, 146, the program will assign a triage level, or upgrade a preliminarily assigned triage level, if necessary to arrive at a final triage level assignment for the patient. As indicated by box 148, if the medical professional desires, the program assigned level can be overridden to increase the priority of the patient's triage level assignment, but for safety reasons, a program assigned level can not be overridden to downgrade the priority of the patient's triage level assignment. As shown in box 150, this ends the triage process for all patients who are thirteen (13) years of age or older.

Pediatric Process

Beginning at A box 54 of FIG. 1-B, the pediatric initial screening algorithm 50 begins by entering the patient's name 64 or social security number 66 and date of birth 70, as shown in box 200. Then the patient's vital signs are entered, as shown by box 202. There is a * located between boxes 200 and 202 indicating that from this point forward in the process there are several optional routes for performing the remaining steps of the triage process. Those optional routes are illustrated in FIG. 2 and will be described in more detail hereafter. Continuing at box 202 FIG. 1-B, after the patient's vital signs are entered into the computer, the program then does level I vital signs determination, as shown in box 204, based on whether the vital signs are abnormal for the particular age of the child.

The level I vital signs determination 204 inquires whether the oxygen saturation is below normal based on the patient's age and either the patient's heart rate or respiratory rate is abnormal for their age. If the answer is yes to this box 204 inquiry, as shown in box 206, a level 1 priority is assigned to the patient in box 208 and the process ends in box 210. On the other hand, if the answer is no to box 204 inquiry, as shown in box 212, a level II vital signs determination is done, as shown in box 214.

The level II vital signs determination 214 inquires whether both the heart rate and the respiratory rate are abnormal based on the patient's age, or alternately, the oxygen saturation is below normal based on the patient's age. If the answer to the level II vital signs determination 214 is yes, as shown in box 216, a priority level of not less than II is assigned, as shown in box 218, and the process continues at box 220 where critical level I observations occur. If the answer to the level II vital signs determination 214 is no, as shown in box 222, the level III vital signs determination is done, as shown in box 224.

If the answer to the level III vital signs determination is yes, as shown in box 226, a priority level of not less than III is assigned, as shown in box 228, and the process continues at box 220. If the answer to the level III vital signs determination 224 is no, as shown in box 230, the process continues at box 220.

In box 220, the critical level I observations inquire whether the child is limp or unresponsive; cyanotic, grunting, or retracting; or actively seizing. If the answer to the critical level 1 observations 220 is yes, as shown in box 232, a level I priority is assigned to the patient, as shown in box 208 and the process ends, as shown in box 210. If the answer to the critical level 1 observations 220 is no, as shown in box 234, level II observations are made, as shown in box 236.

The level II observations 236 inquire whether the child has a petechiael or purpuric rash or whether the medical professional suspects child abuse. If the answer to the level II observations 236 is yes, as shown in box 238, a level II is assigned to the patient, as shown in box 240, and the process ends, as shown in box 242. If the answer to the level II observations 236 is no, as shown in box 244, the next inquiry, as shown in box 246, is whether the child's age is 3 months or less. If the answer to this age question is yes, as shown in box 248, the next inquiry, as shown in box 250 is whether the patient's temperature is above 100.4 degrees Fahrenheit. If the answer to this temperature question 250 is yes, as shown in box 252, the patient is assigned a priority level of II, as shown in box 254 and the process ends, as shown in box 256. If either the answer to the age question of box 246 is no, as shown in box 258, or the answer to the temperature question of box 250 is no, as also shown by box 258, the process continues at C box 260 on FIG. 1-D, as indicated by the Go to C box 262 of FIG. 1-B.

All of the process shown in FIG. 1-D is a subpart of the larger pediatric initial screening algorithm 50. The process continues, as shown in box 264 with a determination of the child's chief complaint. Next, as shown in box 266, one of approximately forty seven (47) specific pediatric algorithms is selected based on the child's chief complaint 264. Those pediatric algorithms are shown in FIG. 9.

Next, as shown in box 268, the patient and/or the patient's parent answer the questions of the selected algorithm which results in the assignment of a triage level to the patient based on the answers to the interview questions, as shown in box 270. The medical professional can optionally upgrade the patient's triage level if desired, as shown in box 272, and the process ends, as shown in box 274.

Flexible Routes and Reports

Now that system 10 has been described in use for an adult patient and for a pediatric patient, the flexibility of the system 10 will be described. Referring to FIG. 2, there are illustrated three pathways, indicated by Arrows 1, 2, and 3, that can be employed in entering the vital signs information on a patient within the present system 10. As shown by the *located in the Start box 300 in FIG. 2, this portion of the process can be used either beginning in the process at the * illustrated in FIG. 1-B for a pediatric patient or alternately beginning in the process at the * illustrated in FIG. 1-C for an adult patient.

FIG. 2 shows the three different pathways or sequences that the user can employ in completing the triage. These alternate pathways make it possible to have more than one medical professional working on the triage of a patient, with one medical professional taking the vital signs and the other interviewing the patient. Flexibility of using any of these three pathways in the system 10 allows the triage information to be entered as it is obtained, which is not always in a particular order or sequence for a particular patient and may involve entering specific types of information, such as for example vital signs, into the computer for several patients at a time.

Pathway 1 has already been previously described for both adult and pediatric patients. This is the pathway that is detailed in FIGS. 1-A, 1-C and 1-E for adult patients and that is detailed in FIGS. 1-A, 1-B and 1-D for pediatric patients. Pathway 1 consists of entering the patient's vital signs, as shown in box 302, then completing the interview questions, as shown in box 304, and then determining and assigning the final triage level, as shown in box 306 before the triage process ends, as shown in box 308.

As shown by boxes, 300, 310, 312, 314, 316, 318, 320, 306, and 308, pathway 2 consists of beginning the $2^{nd}$ pathway 300, continuing the algorithm 310, i.e. starting either the pediatric initial screening algorithm if the patient is a child or the chief complaint based algorithm if the patient is not a child, completing the interview questions 312, suspending triage on the patient while another patient is triaged 314, assigning a preliminary triage level based on the answers to the questions 316, waiting for completion of the vital signs 318, entering the vital signs 320, determining and assigning a final triage level 306, and ending the process 308. In this second pathway, the vital signs are entered 320 after the interview has been completed 312.

Likewise, as shown boxes 300, 322, 324, 326, 328, 304, 306, and 308, pathway 3 consists of beginning the $2^{nd}$ pathway 300, entering the patients vital signs 322, suspending triage on the patient while another patient is triaged 324, assigning a preliminary triage level 326, waiting for completion of the interview questions 328, completing the interview questions 304, determining and assigning a final triage level 306, and ending the process 308.

Referring now to FIG. 6, the triage system includes a computer interface so that the emergency department physician has constant real time information on the criticality of each patient that is in the emergency department waiting area, thereby enabling the medical personnel to provide priority attention to those patients that have the most critical conditions. FIG. 6 shows a waiting area screen 162 that the physician can access on a computer to see a list 164 of the patients that are in the waiting area waiting to be brought back into the emergency department, the triage level 166 for each patient, the time 168 each patient arrived at the emergency department, and the patient's chief complaint 170. This waiting area screen 162 can also be used by medical professionals to record whether the patient left without being seen by clicking on the LWOBS column 172, assign a patient to a room in the emergency department by clicking on the Assign/Disposition column 174, or pull up a full triage report on the patient by clicking on the View Report column 176.

Figure 7:
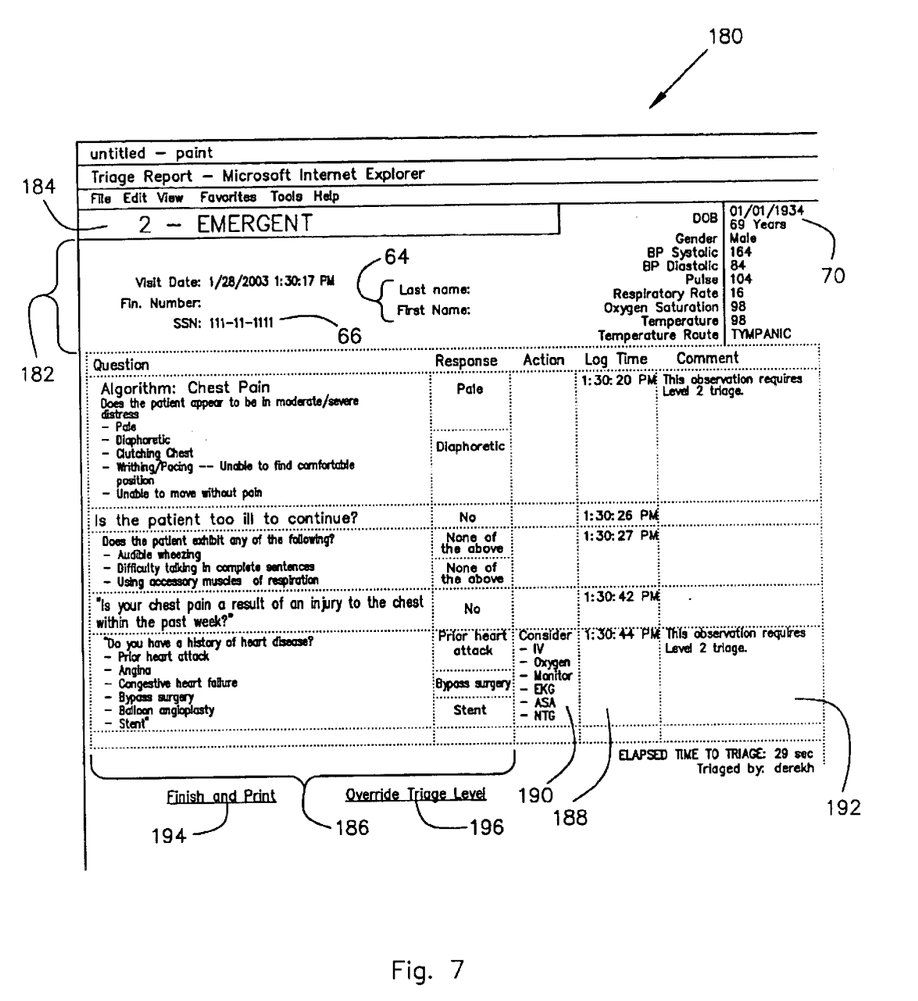
FIG. 7 is a typical patient triage report created by the present system.

FIG. 7 shows a typical triage report 180 for a patient. The top of the report includes the patient information 182 and triage level assignment 184. The triage level 184 is in large print and is color coded to provide a visual indication of priority. Level I is coded by the color red. Level II is orange. Level III is yellow. Level IV is blue, and level V is green. This patient triage report 180 is arranged so that it can be quickly scanned by the physician before he sees the patient. The patient triage report 180 also includes all of the information gathered about the patient during the triage process 186, including the time 188 that the information was gathered. Affirmative answers also appear in red. The report suggests certain actions 190 that might need to be taken and comments 192 on the patient's condition. Actions 190 may be added, deleted, or modified by the local hospital by using an action maintenance tool. At the bottom of the screen, the medical professional has two options. They can finish and print out the report 194 so that it can be used by the physician at the time the physician first sees the patient and placed in the patient's medical file as a permanent record of the triage process for that patient, or they can override the triage level 196 to assign a higher triage level than the system has assigned for a patient.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A medical pathways rapid triage system for conducting triage on patients in an emergency department comprising the following steps:

a. entering level I observations about the patient into a computerized triage system, b. determining based on the level I observations whether the patient should be assigned a level I triage or whether to continue the triage process, c. determining whether the patient is less than 13 years old, d. continuing the triage process if the patient is less than 13 years old by employing a pediatric initial screening algorithm, e. entering the patient's identifier and date of birth into the system, f. entering patient's vital signs into the system, g. determining based on the patient's vital signs whether the patient should be assigned a level I triage and triage ended, assigned no less than level II triage and continue with observations, assigned no less than level III triage and continue with observations, or continue with observations without any triage assignment, h. entering observations into the system, i. determining based on the observations whether the patient should be assigned a level I triage and triage ended, assigned a level II triage and triage ended, or continue with pediatric interview, j. determining the patient's chief complaint, k. selecting an algorithm based on the chief complaint, l. entering the answers to a series of scripted, chief complaint specific questions to elucidate the nature of the patient's problem and the urgency for evaluation, and m. assigning a triage level to the patient based on the information entered into the system.

2. The medical pathways rapid triage system for conducting triage on patients in an emergency department according to claim 1 wherein the pediatric initial screening algorithm further comprises the following optional step:

n. overriding the system to increase the triage level that was previously assigned by the system for the patient based on the judgment of the attending medical professional.

3. A medical pathways rapid triage system for conducting triage on patients in an emergency department comprises the following steps:

a. entering level I observations about the patient into a computerized triage system, b. determining based on the level I observations whether the patient should be assigned a level I triage or whether to continue the triage process, c. determining whether the patient is less than 13 years old, d. continuing the triage process by doing adult triage if the patient is not less than 13 years old, e. determining the patient's chief complaint, f. selecting an algorithm based on the chief complaint, g. entering the patient's identifier and date of birth into the system, h. entering patient's vital signs into the system, i. determining based on the patient's vital signs whether the patient should be assigned a level I triage and triage ended, assigned no less than level II triage and continue with level II observations, assigned no less than level III triage and continue with level II observations, or continue with level II observations without any triage assignment, j. entering level II observations into the system, k. determining based on the level II observations whether the patient should be assigned a level II triage and triage ended, or continue with interview, l. entering the answers to a series of scripted, chief complaint specific questions to elucidate the nature of the patient's problem and the urgency for evaluation, and m. assigning a triage level to the patient based on the information entered into the system.

4. The medical pathways rapid triage system for conducting triage on patients in an emergency department according to claim 3 wherein the adult triage further comprises the following optional step:

n. overriding the system to increase the triage level that was previously assigned by the system for the patient based on the judgment of the attending medical professional.

* * * * *